United States Patent
Eliasson et al.

(10) Patent No.: US 6,375,832 B1
(45) Date of Patent: Apr. 23, 2002

(54) FUEL SYNTHESIS

(75) Inventors: Baldur Eliasson, Birmenstorf; Eric Killer, Wettingen, both of (CH); Chang-Jun Liu, Tianjin (CN)

(73) Assignee: ABB Research Ltd., Zurich (CH)

( * ) Notice: Subject to any disclaimer, the term of this patent is extended or adjusted under 35 U.S.C. 154(b) by 0 days.

(21) Appl. No.: 09/532,082

(22) Filed: Mar. 21, 2000

(30) Foreign Application Priority Data

Mar. 24, 1999 (EP) .............................................. 99810261

(51) Int. Cl.⁷ ....................... C10G 35/04; C10G 35/06; C07C 2/64; C07C 15/067; H05F 3/00

(52) U.S. Cl. ....................... 208/141; 208/134; 208/137; 585/328; 585/446; 585/454; 204/164; 204/168; 204/170

(58) Field of Search ................................ 208/134, 137, 208/141; 583/328, 446, 454; 204/164, 168, 170

(56) References Cited

U.S. PATENT DOCUMENTS

| 5,573,733 | A |   | 11/1996 | Salama |
| 6,045,761 | A | * | 4/2000 | Bill et al. |
| 6,284,105 | B1 | * | 9/2001 | Eliasson et al. |
| 6,284,157 | B1 | * | 9/2001 | Eliasson et al. |

FOREIGN PATENT DOCUMENTS

| DE | 242 007 |   | 1/1987 |
| DE | 42 20 865 |   | 2/1993 |
| EP | 0 899 010 |   | 3/1999 |
| WO | WO-01/70652 A1 | * | 9/2001 |

OTHER PUBLICATIONS

Keyser et al., "Fischer–Tropsch Studies with Cobalt–Manganese Oxide Catalysts: Synthesis Performance in a Fixed Bed Reactor", *Elsevier Schience B.V.*, Applied Catalysis A: General 171, 1998, pp. 99–107.

Crabtree, "Aspects of Methane Chemistry", *Chem. Rev.*, 1995, 95, pp. 987–1007.

Gesser et al., "The Direct Conversion of Methane to Methanol by Controlled Oxidation", *Chemical Reviews*, vol. 85, No. 4, Aug. 1985, pp. 235–244.

Eliasson et al., "Modeling and Applications of Silent Discharge Plasmas", *IEEE Transactions on Plasma Science*, vol. 19, No. 2, Apr. 1991, pp. 309–323.

Wokaun et al., "Greenhouse Gas Chemistry", *Energy Convers. Mgmt.*, vol. 38, Suppl., 1997, pp. S415–S422.

* cited by examiner

Primary Examiner—Walter D. Griffin
Assistant Examiner—Tam M. Nguyen
(74) Attorney, Agent, or Firm—Blank Rome Comisky & McCauley LLP

(57) ABSTRACT

A method of transforming a normally gaseous composition containing at least one hydrogen source, at least one oxygen source and at least one carbon source into a normally liquid fuel, wherein said gaseous composition consists at least in part of carbon dioxide as said carbon source and said oxygen source, and of methane as said hydrogen source and as a second carbon source; the method comprising the steps of feeding the composition into a reactor including a first electrode means, a second electrode means and at least one layer of a normally solid dielectric material positioned between the first and the second electrode means; submitting the composition within the reactor in the presence of a normally solid catalyst to a dielectric barrier discharge, wherein said normally solid catalyst is a member selected from the group of zeolites, aluminophosphates, silicoaluminophosphates, metalloaluminophosphates and metal oxides containing OH groups; and controlling the dielectric barrier discharge to convert the gaseous composition into the normally liquid fuel.

8 Claims, 1 Drawing Sheet

FUEL SYNTHESIS

BACKGROUND OF THE INVENTION

1. Field of the Invention

The present invention relates to a method of transforming a normally gaseous composition containing at least one hydrogen source, at least one oxygen source and at least one carbon source into a normally liquid fuel, furthermore the present invention relates to a normally liquid fuel and to an apparatus for transforming a normally gaseous composition into a normally liquid fuel.

One of the major problems facing mankind is the global warming of the atmosphere due to man-made emissions of greenhouse gases such as carbon dioxide, methane, chlorofluorocarbons, nitrous oxide or ozone. One possible approach to mitigate the emissions of these greenhouse gases to the atmosphere would be to recycle them in a chemical process to form useful products. Among all the man-made greenhouse gases, methane and carbon dioxide contribute to most of the greenhouse effect.

2. Description of Related Art

Intensive investigations have been carried out either to convert methane into higher hydrocarbons by oxidative coupling of methane as well as to convert methane into methanol by partial oxidation of methane (reports of R. H. Crabtree et al. in Chem. Rev. 95 (1995) 987 and of H. D. Gesser, N. R. Hunter and C. B. Prakash in Chem. Rev. 85 (1985) 235; both reports being incorporated herein for all purposes by way of reference). However, the yield of objective products from these conventional catalytic methane conversions is too low for a practical application.

A great effort has also given to chemical fixation of carbon dioxide. Heterogeneous catalysis has been considered to be a desirable route for carbon dioxide utilization. But a large amount of additional energy or expensive hydrogen is required for conventional catalytic utilization of carbon dioxide since the carbon dioxide molecule has a very low energy content. There is still no confirmed technology by far for utilizing such a plentiful carbon source.

A few processes for the synthesis of liquid fuel starting from gaseous compositions are known, such as the "Mobil process" and the "Fischer-Tropsch process" schematically shown in equation (1) and (2).

For both heterogeneous catalyzed processes the production of "synthesis gas", a mixture of CO and $H_2$ also named "syngas", represents the first step along the path to methanol and gasoline respectively. Even if the "Mobil process" (eq. (1)) and the "Fischer-Tropsch process" (eq. (2)) are practiced today for industrial fuel synthesis production, e.g in South Africa, Malaysia and New Zealand, they are non-economic "political processes", heavily supported by governmental subsidies. The lack of profitableness is either due to the usually required high pressures at which the processes take place as well as to the high production costs of syngas and the fact that the produced syngas needs to be compressed before applied in the processes (1) and (2). Thus, about 60% to 80% of the total cost of the processes (1) and (2) goes to production and compression of syngas.

The industrial production of syngas mostly derives from the energy-intensive steam reforming of methane shown in equation (3):

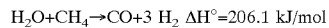

Syngas can also be produced from the greenhouse gases methane and carbon dioxide as shown in equation (4). However, such a reforming of carbon dioxide by methane is also a very energy-intensive process and requires high temperatures. Moreover, deposition of carbon on the catalyst always causes problems for this reaction.

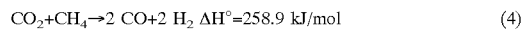

Non-equilibrium plasma chemical processes occuring in the volume part of electrical non-equilibrium discharges have attracted a great deal of interest. Particularly, silent gas discharges have demonstrated its suitability for large-scale industrial applications. The ozone generation, as its most important industrial application so far, is described by Eliasson et al. in IEEE Transactions on Plasma Science, Vol. 19 (1991), page 309–323 (this report being incorporated herein for all purposes by way of reference). It is to be noted that a characteristic of the silent discharge is the presence of a dielectric. Therefore silent gas discharges are also referred to as dielectric barrier discharges.

Recently, the utilization of greenhouse gases for the synthesis of methanol or methane in such silent gas discharge reactors has also been described. Thus, DE 42 20 865 describes a method and an apparatus for the hydrogenation of carbon dioxide leading in particular to methane or methanol by exposing a mixture of carbon dioxide and a substance containing hydrogen atoms, preferably hydrogen or water, to a dielectric barrier discharge. An overview of the progress in this field have been summarized by Eliasson et al. in Energy Conversion Management 38 (1997) 415 (this report being incorporated herein for all purposes by way of reference). It is noteworthy, however, that the reported maximum yield of methanol was only about 1%.

SUMMARY OF THE INVENTION

Accordingly, it is an object of the present invention to provide for a method of transforming a normally gaseous composition into a normally liquid fuel, which method can be carried out economically, preferably at low pressures.

It is another object of the present invention to provide for a method of producing liquid fuel from gaseous compositions in reasonable yields and in a direct manner, i.e. making the expensive formation of syngas no longer necessary.

Another object of the present invention is to provide for an apparatus that allows the transformation of a gaseous composition into a liquid fuel.

Further objects and advantages of the present invention will become apparent as this specification proceeds.

THE INVENTION

Accordingly, the invention provides for a method of transforming a normally gaseous composition containing at least one hydrogen source, at least one oxygen source and at least one carbon source into a normally liquid fuel, wherein the gaseous composition consists at least in part of carbon dioxide as the carbon source and the oxygen source, and of methane as the hydrogen source and as a second carbon source, which method comprises the steps of feeding the gaseous composition into a reactor that includes a first electrode means, a second electrode means and at least one layer of a normally solid dielectric material positioned between said first and said second electrode means, submitting the composition within the reactor to a dielectric barrier discharge in the presence of a normally solid catalyst, wherein said normally solid catalyst is a member selected from the group of zeolites, aluminophosphates, silicoaluminophosphates, metalloaluminophosphates and metal oxides containing OH groups, and controlling the dielectric barrier discharge to convert the gaseous composition into the normally liquid fuel. Typically, the normally solid catalyst is selected from the group commonly designated as shape-selective catalysts.

In a second general embodiment the invention provides for a normally liquid fuel obtainable by a dielectric barrier discharge, the normally liquid fuel comprising at least 60 mol % of hydrocarbons having a normal boiling range of between about 50° C. and about 210° C., and less than 10 mol % of oxygenated hydrocarbons.

In a third general embodiment the invention provides for an apparatus for transforming a normally gaseous composition containing at least one hydrogen source, at least one oxygen source and at least one carbon source into a normally liquid fuel as set forth in claim 9.

BRIEF DESCRIPTION OF THE DRAWINGS

For a better understanding of the nature and scope of the present invention—and not to limit the invention—preferred embodiments and details of the inventive method and apparatus are described in more detail in the following by reference to the drawings, in which.

DETAILED DESCRIPTION OF THE INVENTION

Figure 1:
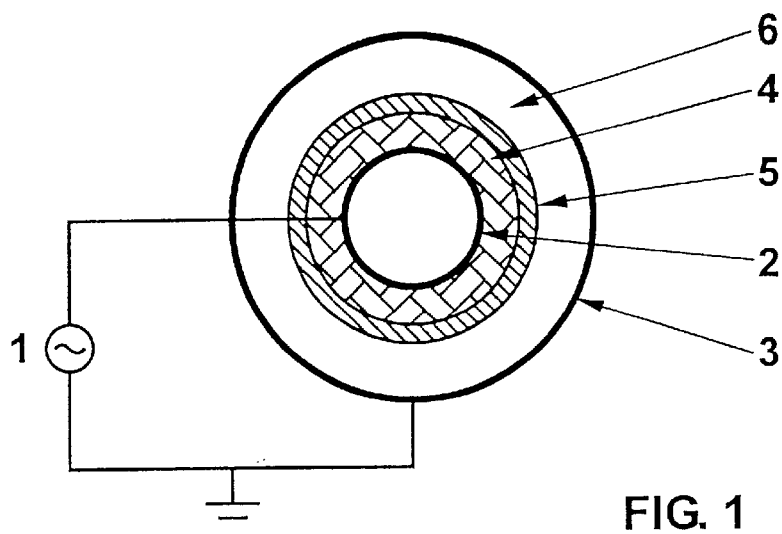
FIG. 1 is a diagrammatic cross sectional view of a preferred dielectric barrier discharge reactor configuration according to the invention.

The term "about" as used herein before any numeral implies a variation of typically ±10%.

The term "normal" with regard to boiling points, boiling ranges, physical states of matter and the like indicates that the value is understood as being corrected for "normal conditions", i.e. a temperature of 25° C. and an atmospheric pressure of 1013 mbar.

The term "layer" is used herein to refer to any planar or curved stratum having a width dimension that is substantially larger than its thickness dimension; typically, the width:thickness ratio is at least 10:1 and generally well above that value.

Sources of gaseous compositions containing methane and/or carbon dioxide are for example fermentation gas, natural gas or any waste and exhaust gases deriving from industrial processes and containing methane and/or carbon dioxide. It is, however, in accordance with and within the scope of the present invention to use commercially available methane and carbon dioxide of any purity or any other source of methane and/or carbon dioxide known to the man skilled in the art.

According to a preferred embodiment of the present invention the molar ratio of carbon dioxide and methane $CO_2:CH_4$ is between about 1:1 to about 1:4, preferably between about 1:2 to about 1:3.

The preferred solid catalyst is a zeolite selected from the group of zeolite X, zeolite Y, zeolite A, zeolite ZSM-5 and zeolite 13X.

In a further preferred embodiment of the invention, the normally solid catalyst comprises at least one substance selected from the group of metal ions and group IA, IIa, IB, IIb and VIII elements of the periodic table. The latter mentioned elements, i.e. alkali, earth alkali elements as well as the elements of the zinc and the copper group and the iron groups of the periodic table can be present either in ionic or atomic form. Those normally solid catalysts are synthesized by procedures generally known to the man skilled in the art, such as any type of ion exchange reactions in the case of zeolites. Examples of those solid catalysts are the zeolites NaY, NaX, NaA or Fe-ZSM-5.

Particularly, the use of zeolites as the normally solid catalyst limits the growth of the hydrocarbon chain and thus inhibits the undesired formation of solid polymer. Consequently, an increased production and yield respectively of liquid fuel results. Moreover, applying "shape-selective catalysts", such as zeolites, leads to a large amount of branched hydrocarbons representing a higher-quality fuel.

The term "shape-selective catalyst" is intended to refer to a catalyst that owns a special structure to limit the diffusion of the reacting molecules and the formed product molecules through its framework. Only molecules with diameters smaller than the openings or pores of the shape-selective catalyst can pass through the catalyst. Moreover, an additional constraint is imposed by the size and shape of the pores with respect to possible transition states of the reaction.

Furthermore, the use of zeolites as the normally solid catalyst offers the advantage of having high concentrations of OH groups on the zeolite surfaces, i.e. on the outer surfaces of the zeolite as well as within the zeolite cavities. In addition to the high concentration of OH groups on zeolite surfaces, an important characteristic of zeolites is the natural coulombic field formed within the zeolite framework. Within this context, it should be noted that both the concentration of OH groups and the strength of the natural coulombic field are controllable and adjustable. Generally, these two features allow the zeolites to easily respond to an external electric field, i.e. the zeolite becomes electrically charged more easily. The control of the dielectric barrier discharge according to the invention allows though to control these charges and electrostatic fields and, therefore, to control zeolite activity and selectivity in the conversion of a gaseous composition into a normally liquid fuel.

Typically, an operating pressure in the range of from about 0.1 bar to about 30 bar at an operating temperature up to about 400° C. is maintained in the reactor.

Preferably, the layer of the normally solid dielectric material has a thickness of between about 0.1 mm to about 5 mm and the dielectric constant of the normally solid dielectric material is between about 2 to about 20.

In another preferred embodiment of the invention, the normally solid dielectric material is at least partially formed by the normally solid catalyst.

The normally liquid fuel obtainable by a dielectric barrier discharge comprises at least 60 mol % of hydrocarbons, typically at least 90 mol % of hydrocarbons, and preferably at least 95 mol % of hydrocarbons having a boiling range of between about 50° C. and about 210° C., typically between about 50° C. and about 180° C. and a ratio branched hydrocarbons:linear hydrocarbons of higher than 6:1, typically about 9:1. The normally liquid fuel generally contains less than 10 mol % of oxygenated hydrocarbons, such as methanol, ethanol or higher, typically branched oxygenates. Typically, the normally liquid fuel comprises less than 5 mol % and preferably less than 2 mol % of oxygenated hydrocarbons. In particular, the selectivity towards methanol is generally less than 2 mol %, typically less than 1 mol % and preferably less than 0.5 mol %.

In a preferred embodiment of the apparatus according to the invention the normally solid catalyst is a member selected from the group of zeolites, aluminophosphates, silicoaluminophosphates, metalloaluminophosphates and metal oxides containing OH groups. Preferably, the normally solid catalyst is a zeolite being a member selected from the group of zeolite X, zeolite Y, zeolite A, zeolite ZSM-5, zeolite 13X.

In another preferred embodiment of the inventive apparatus, the normally solid catalyst comprises at least one substance selected from the group of metal ions and group IA, IIa, IB, IIb and VIII elements of the periodic table.

Typically, the layer of the normally solid dielectric material has a thickness of between about 0.1 mm to about 5 mm. The dielectric material has preferably a dielectric constant of between about 2 to about 20.

In a further preferred embodiment of the inventive apparatus, the first electrode means has a first effective electrode surface and the second electrode means has a second effective electrode surface, the at least one layer of the normally solid dielectric material covering at least a portion of the effective surface of at least one of the first and the second electrode means, the normally solid catalyst covering at least a portion of the layer of the normally solid dielectric. Typically, the first and the second electrode means each have an essentially tubular form, one of the first and the second electrode means forming an outer shell while the other of the first and the second electrode means forms an inner shell; the inner shell being distanced from the outer shell by an essentially tubular gap; the at least one layer of the normally solid dielectric material being arranged in an essentially tubular form and covering at least a portion of the inner and/or the outer shell; the normally solid catalyst being arranged in an essentially tubular form and covering at least a portion of the at least one layer of the normally solid dielectric. Preferably, the tubular form is essentially cylindrical.

In another preferred embodiment of the inventive apparatus, the first and the second electrode means each are provided by at least one essentially planar structure, the first electrode being distanced from the second electrode means by at least one essentially planar gap; the at least one layer of the normally solid dielectric being provided by at least one essentially planar structure and covering at least a portion of the first and/or the second electrode means; the normally solid catalyst being provided by at least one essentially planar form and covering at least a portion of the at least one layer of the normally solid dielectric material.

Typically, a plurality of pairs of first and said second electrode means are arranged in an essentially parallel or staked configuration forming a plurality of gaps, the gaps being connected in series to form an elongated path for passage of said normally gaseous mixture.

In a further preferred embodiment of the inventive apparatus, the normally solid dielectric material is at least partially formed by the normally solid catalyst.

The dielectric barrier discharge is a high pressure non-equilibrium discharge which occurs when alternating voltages are applied to a gas space between tow electrodes separated by a non-conducting medium. FIG. 1 shows schematically a cross sectional view of a dielectric barrier discharge reactor according to the invention. The high voltage AC generator 1 is connected to the first electrode 2 and to the second grounded electrode 3 both having an essentially cylindrical form. The electrodes are generally made of corrosion-resistant metals or alloys or of materials covered by at least one layer of an electrically conducting substance. Electrode 2 forms an outer shell and Electrode 3 forms an inner shell. The dielectric layer 4 is typically a glass, quartz or ceramic tube having a thickness of between about 0.1 mm and about 5 mm and covers the effective surface of electrode 2. The shape-selective catalyst 5 shown in FIG. 1, is also formed in essentially cylindrical form and is provided to cover the dielectric layer 4. Typically, the dielectric tube 4 serves as support for the solid catalyst 5. So, the solid catalyst, 5 typically in powder form, is disposed in a piece of gas-permeable quartz fleece and wrapped around the outer surface of the dielectric tube 4, i.e. the surface of the dielectric tube 4 facing towards the electrode 3. Further catalyst support arrangements preferably used for the present dielectric barrier discharge reaction are described in EP-899,010 (the disclosure of which being incorporated herein for all purposes by way of reference). It is obvious that the form and the size of the solid catalyst, i.e. whether it is applied in powder form or as grains of different sizes and the manner by which the catalyst is supported, i.e by means of the dielectric material and by means of an additional support respectively, can be modified within the scope of the present invention.

The normally gaseous composition passes through the essentially cylindrical discharge gap 6, where it is exposed to the dielectric barrier discharge. The dielectric barrier discharge is effected by an AC potential applied between the first electrode and the second electrode means. The preferred AC potential being in the range of from about 6 kV to about 100 kV and the frequency of the AC potential preferably being in the range of from about 50 Hz to about 1 MHz. The dielectric barrier discharge is controlled by maintaining a current density in the range of between about 0.1 A/m$^2$ and about 10 A/m$^2$ as calculated for the effective surface of one of the first and second electrodes. As indicated above, an operating pressure in the range of from about 0.1 bar to about 30 bar at an operating temperature up to about 400° C. is maintained in the reactor. The normally gaseous mixture is passed through said reactor preferably at a rate of from about 0.1 m$^3$/hour to about 200 m$^3$/hour.

When the amplitude of applied AC electric field reaches a critical value, breakdown is initiated in the gas and a current flows from one electrode to the other. Once breakdown is initiated at any location within the discharge gap, charge accumulates on the dielectric leads to formation of an opposite electric field. This opposite electric field reduces the external electric field within the gap and interrupts the current flow in a few nanoseconds to form microdischarges. The duration of the current pulse relates to pressure and properties of gases involved and the dielectrics applied. A large number of such microdischarges will be generated when a sufficiently high AC voltage is applied. The principal advantages of dielectric barrier discharge are: it combines the large volume excitation of glow discharges with high pressure characteristics of corona discharges; the entire electrode area is effective for discharge reactions.

Figure 2:
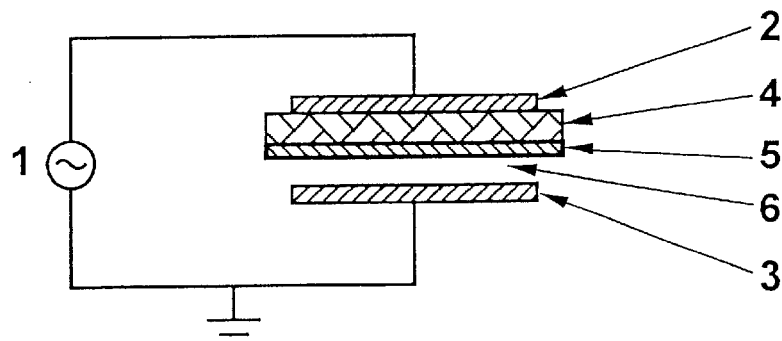
FIG. 2 is a diagrammatic cross sectional view of a further preferred dielectric barrier discharge reactor configuration according to the invention.

FIG. 2 shows another preferred configuration of a dielectric barrier discharge reactor according to the invention. The corresponding electrodes, the layer of the normally solid dielectric material and the normally solid catalyst respectively of this embodiment have or are arranged in an essentially planar form. Examples of the dielectric material are glass, as indicated, as well as quartz, ceramics, $ZrO_2$ or $Al_2O_3$.

Further preferred dielectric barrier discharge reactor configurations not being shown in the FIGS. 1 and 2 are those, where the solid catalyst either occupies an essential part of the discharge gap 6 or where the solid catalyst covers only a portion of the dielectric material.

Figure 3:
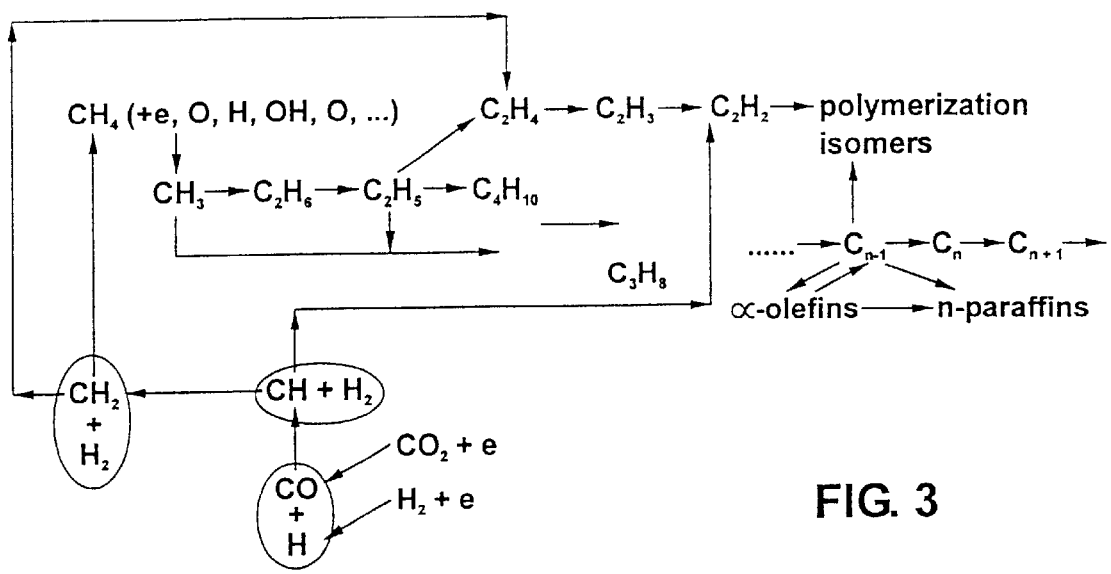
FIG. 3 is a schematic representation of possible hydrocarbon chain growth pathways occurring in the preferred transformation of methane and carbon dioxide in a DBD reactive system according to the invention.

While not wishing to be bound by any specific theory for explaining the findings which led to the present invention, the following consideration is presented:

The inventive method discloses the formation of a liquid fuel, preferably higher hydrocarbons starting from a normally gaseous composition, preferably methane and carbon dioxide thus making the expensive formation of syngas no longer necessary. It is considered that methyl radicals are responsible for the initiation of these free radical chain reactions. The hydrocarbon chain growth pathways are also very similar to pathways found in Fischer-Tropsch synthesis. This could suggest a very important new pathway for direct hydrocarbon formation at atmospheric pressure via dielectric barrier discharge. FIG. 3 shows a schematically representative of free radical chain pathways.

Another important finding is that the CO selectivity did not increase with a significantly increasing in conversion of carbon dioxide, while CO formation can be explained from electron disssociation or dissociative attachment of carbon dioxide in the plasma discharges. It seems to be that the new formed CO will continue to react with plasma species to produce hydrocarbons. FIG. 3 also shows a possible pathway for this hydrocarbon formation. It can be expected that the new formed CO will take some extra energy from discharge reactions and will be much easier to further react with plasma species like H, compared to CO in ground state with the catalytic F-T synthesis. On the other hand, the dissociation reactions for CO production from carbon dioxide will generate oxygen species at the same time. Some oxygen species like O and O($^1$D) are very efficient for generation of methyl radicals. O($^1$D) is also active for methanol formation from methane.

EXAMPLE 1

The feed gases, i.e. a mixture containing 50% methane and 50% carbon dioxide, were introduced into the system flowing downstream through the reactor. The flow rate is 200 ml/min. The catalyst used is 13X zeolite. An alternating voltage of about 10 kV with a frequency of about 30 kHz is applied to the electrodes. A dielectric barrier discharge is thus initiated. The operating temperature is maintained at about 200° C. and the operating pressure is about 11 kPa. A back pressure valve at the exit of the reactor was used to adjust the pressure. A MTI (Microsensor Technology Inc., M20011) dual-module micro gas chromatograph containing a Poraplot Q column and a molecular sieve 5A Plot column with a TCD detector was used to detect gaseous products. The gas sample was heated by a heated line to avoid possible condenstaion before it was taken into the GC. The liquid sample was also gas-chromatographically analysed. The results of the synthesis are reported in Table 1, wherein the conversion of methane and carbon dioxide respectively are defined as:

Conversion $[CH_4]=\{([CH_4]_{in}-[CH_4]_{out})/[CH_4]_{in}\}\times 100\%$ and

Conversion $[CO_2]=\{([CO_2]_{in}-[CO_2]_{out})/[CO_2]_{in}\}\times 100\%$ respectively. The selectivity of the products are defined as:

Selectivity $[prod.]=\{$(number of carbon atoms of prod.$\times[prod.]_{out})/$ total carbon amount converted$\}\times 100\%$ The analysis of the gas sample reveals formation of carbon monoxide CO, alkanes having 2 to 5 carbon atoms (C2–C5) such as iso-butane and iso-pentane, unsaturated hydrocarbons such as ethylene and acetylene, small amount of oxygenated products such as $CH_3OCH_3$, methanol and ethanol as well as water and hydrogen. The analysis of the liquid sample shows a high yield of gasoline components (C5–C11) being rich in branched hydrocarbons. The ratio branched:linear hydrocarbons is about 9:1.

In Table 1, results from recently reported catalytic Fischer-Tropsch synthesis (M. J. Keyser, R. C. Everson and R. L. Espinoza in Applied Catalysis A, Vol. 171 (1998) 99; this report being incorporated herein for all purposes by way of reference) are additionally listed for sake of comparison. Evidently, the product distribution is very similar for both processes, i.e. obtained by the inventive dielectric barrier discharge synthesis (DBD synthesis) and the Fischer-Tropsch synthesis (F-T synthesis). However, the inventive method operates at low or atmospheric pressures, whereas Fischer-Tropsch synthesis is performed at very high pressures.

TABLE 1

Synthesis performance results

|  | Catalytic F-T-synthesis | our DBD Synthesis |
|---|---|---|
| gas temperature (° C.) | 220 | 202 |
| gas pressure (kpa) | 500 | 11 |
| $H_2$/CO | 1/1 |  |
| $CH_4$/$CO_2$ |  | 1/1 |
| Bed length (m) | 0.25 | 0.30 |
| GHSV ($h^{-1}$) | 222 |  |
| Flowrate (ml/min) |  | 200 |
| Power (w) |  | 500 |
| CO conversion (%) | 14.0 |  |
| $CO_2$ conversion (%) |  | 47.5 |
| $CH_4$ conversion (%) |  | 48.8 |
| carbon atom selectivity (%) |  |  |
| CO |  | 27.9 |
| $C_1$ | 10.8 |  |
| $C_2$ | 5.4 | 8.9 |
| $C_3$ | 14.1 | 3.7 |
| $C_4$ | 9.2 | 1.0 |
| $C_5^+$ | 50.5 | 58.2 |
| $C_1$—OH | 2.0 | 0.26 |
| $C_2$—OH | 3.8 | 0.00 |
| 1-$C_3$—OH | 2.6 |  |
| 1-$C_4$—OH | 0.4 |  |
| $C_5^+$—OH | 0.19 |  |

EXAMPLE 2

A gas mixture containing 80% methane and 20% carbon dioxide is passing through the gap between the electrodes with the catalyst layer. The flow rate is 0.5 Nl/min. The catalyst used is 13X zeolite. An alternating voltage of about 10 kV with a frequency of about 30 kHz is applied to the electrodes. A dielectric barrier discharge is thus initiated. The operating temperature is maintained at about 150° C. and the operating pressure is about 1 bar. The product essentially consists of liquid fuel (C5 to C11), syngas (CO/H2) and light gaseous hydrocarbons (C2 and C3). The liquid fuel product, which is rich in branched hydrocarbons, is collected in a condenser. Similar conversions and selectivities as reported for Example 1 are found.

EXAMPLE 3

The feed gases, i.e. a mixture containing 66.7% methane and 33.3% carbon dioxide, were introduced into the system flowing downstream through the reactor. The flow rate is 150 ml/min. The catalyst used is 13X zeolite. An alternating voltage of about 10 kV with a frequency of about 30 kHz is applied to the electrodes. A dielectric barrier discharge is thus initiated. The operating temperature is maintained at about 150° C. and the operating pressure is about 25 kPa. Under such conditions, methane conversion is 39.5% and carbon dioxide conversion is 33.8%. The selectivities for the products are:

|     |       |
|-----|-------|
| CO  | 32.6% |
| C2  | 17.5% |
| C3  | 12.9% |
| C4  | 6.6%  |
| C5+ | 29.3% |

The success in the research and development of a feasible utilization of greenhouse gases, in particular methane and carbon dioxide, which led to the present invention signify the attainment of two important objectives: First, slowing down a build-up of greenhouse gases in the atmosphere and, second, better carbon resource utilization. An extra advantage of such an utilization of these major greenhouse gases is the fact that such synthesized liquid fuel does not contain pollutants like sulfur that are usually present in coal and petroleum.

Although certain preferred embodiments of the invention have been described herein, it will be apparent to those skilled in the art to which the invention pertains that modifications and variations of the described embodiments may be made without departing from the spirit and scope of the invention.

What is claimed is:

1. A method of transforming a normally gaseous composition containing at least one hydrogen source, at least one oxygen source and at least one carbon source into a normally liquid fuel, wherein said gaseous composition comprises carbon dioxide as said carbon source and said oxygen source, and comprises methane as said hydrogen source and as a second carbon source, said method comprising the steps of:

feeding said composition into a reactor including a first electrode means, a second electrode means and at least one layer of a normally solid dielectric material positioned between said first and said second electrode means;

submitting said composition within said reactor in the presence of a normally solid catalyst to a dielectric barrier discharge, wherein said normally solid catalyst is a member selected from the group consisting of zeolites, aluminophosphates, silicoaluminophosphates, metalloaluminophosphates and metal oxides containing OH groups; and controlling said dielectric barrier discharge to convert said gaseous composition into said normally liquid fuel.

2. The method of claim 1 wherein said carbon dioxide and said methane are contained in said gaseous composition at a molar ratio of carbon dioxide:methane of between about 1:1 to about 1:4.

3. The method of claim 1 wherein said normally solid catalyst is a member selected from the group consisting of zeolite X, zeolite Y, zeolite A, zeolite ZSM-5 and zeolite 13X.

4. The method of claim 1 wherein said normally solid catalyst comprises at least one substance selected from the group consisting of metal ions and group IA, IIa, IB, IIb and VIII elements of the periodic table.

5. The method of claim 1 wherein said layer of said normally solid dielectric material has a thickness of between 0.1 mm to about 5 mm, and wherein said normally solid dielectric material has a dielectric constant of between about 2 to about 20.

6. The method of claim 1 wherein said normally solid dielectric material comprises said normally solid catalyst.

7. The method of claim 1 wherein an operating pressure in the range of from about 0.1 bar to about 30 bar at an operating temperature up to about 400° C. is maintained in said reactor.

8. The method of claim 2, wherein the carbon dioxide and the methane are contained in the gaseous composition at a molar ratio of carbon dioxide:methane of between about 1:2 to about 1:3.

* * * * *